United States Patent
Nieto Magro et al.

(10) Patent No.: US 11,278,491 B2
(45) Date of Patent: Mar. 22, 2022

(54) PROGESTERONE INTRAVAGINAL DEVICES

(71) Applicant: ITF RESEARCH PHARMA, S.L.U., Madrid (ES)

(72) Inventors: Concepción Nieto Magro, Madrid (ES); Elena Pérez Hernando, Madrid (ES); Jaime Moscoso Del Prado, Madrid (ES); Javier Suárez Almarza, Madrid (ES)

(73) Assignee: ITF Research Pharma, S.L.U., Alcobendas-Madrid (ES)

( * ) Notice: Subject to any disclaimer, the term of this patent is extended or adjusted under 35 U.S.C. 154(b) by 0 days.

(21) Appl. No.: 16/982,805

(22) PCT Filed: Mar. 21, 2019

(86) PCT No.: PCT/EP2019/057074
§ 371 (c)(1),
(2) Date: Sep. 21, 2020

(87) PCT Pub. No.: WO2019/180133
PCT Pub. Date: Sep. 26, 2019

(65) Prior Publication Data
US 2021/0030666 A1 Feb. 4, 2021

(30) Foreign Application Priority Data
Mar. 21, 2018 (EP) ..................... 18382190

(51) Int. Cl.
A61K 9/00 (2006.01)
A61K 31/57 (2006.01)
A61K 47/34 (2017.01)

(52) U.S. Cl.
CPC ............ *A61K 9/0036* (2013.01); *A61K 31/57* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 4,816,257 A | 3/1989 | Buster | |
| 6,476,079 B1 * | 11/2002 | Jukarainen | A61P 15/00 514/772.4 |
| 2009/0202612 A1 | 8/2009 | Ahmed et al. | |

FOREIGN PATENT DOCUMENTS

WO  WO 2019/180133 A1  9/2019

OTHER PUBLICATIONS

European Search Report dated Sep. 21, 2018 in connection with European Patent Application No. EP18382190.
"Folleto De Informacion Al Paciente: Fertiring, Progesterona, Anillo Vaginal 1 g." Laboratorios Silesia S.A.
Heredia, V. et al. "Polyisoprene matrix for progesterone release: In vitro and in vivo studies," International Journal of Pharmaceutics, Elsevier, NL, vol. 382, No. 1-2, Dec. 1, 2009, pp. 98-103.
International Preliminary Report on Patentability dated Sep. 22, 2020, including Written Opinion of the International Searching Authority dated Jun. 21, 2019, in connection with PCT International Application No. PCT/EP2019/057074.
International Search Report dated Jun. 21, 2019 in connection with PCT International Application No. PCT/EP2019/057074.
Written Opinion (form PCT/ISA/237) dated Jun. 21, 2019 in connection with PCT International Application No. PCT/EP2019/057074.

* cited by examiner

*Primary Examiner* — Patricia Duffy
*Assistant Examiner* — Garen Gotfredson
(74) *Attorney, Agent, or Firm* — Gary J. Gershik; Amster Rothstein & Ebenstein LLP

(57) ABSTRACT

The invention relates to intravaginal devices, in particular rings, comprising progesterone in a particular polymorphic purity, methods for making such devices and therapeutic uses of said devices. In particular, the intravaginal devices comprise a high amount of progesterone polymorph I and are useful in the treatment of infertility in a female subject.

17 Claims, 3 Drawing Sheets

PROGESTERONE INTRAVAGINAL DEVICES

RELATED APPLICATIONS

This application is a § 371 national stage of PCT International Application No. PCT/EP2019/057074, filed Mar. 21, 2019, designating the United States and claiming priority of EPO Application No. EP18382190.9, filed Mar. 21, 2018, the contents of each of which are hereby incorporated by reference into this application.

FIELD OF THE INVENTION

The invention relates to intravaginal devices comprising progesterone, process for making such devices and uses of said devices.

BACKGROUND OF THE INVENTION

Progesterone (pregn-4-ene-3,20-dione; $C_{21}H_{30}O_2$) belongs to a class of hormones called progestogens. It is the major naturally occurring steroid and is a precursor in the biosynthesis of other steroids, particularly glucocorticoids, androgens and estrogens.

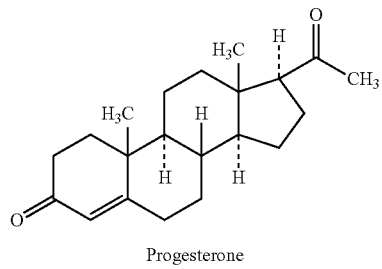

Progesterone

Progesterone is produced in high amounts in the ovaries (by the corpus luteum) from the onset of puberty to menopause, and is also produced in smaller amounts by the adrenal glands after the onset of adrenarche in both males and females. To a lesser extent, progesterone is produced in nervous tissue, especially in the brain, as well as in adipose tissue. During human pregnancy, progesterone is produced in increasingly high amounts by the ovaries and placenta. At first, during the luteal phase or secretory phase of the menstrual cycle and in the early pregnancy, the source is the corpus luteum, however, after the 8th week of pregnancy, production of progesterone shifts to the placenta.

Progesterone readies the uterus for implantation of an embryo, helping the endometrium to be thicker and to become more vascular, preparing it to accommodate the fertilized egg. It also plays several roles in gestation, including breast enlargement of pregnant woman, inhibition of uterine contractility, immunological protection of the embryo, and inhibition of prostaglandin synthesis.

Progesterone has been used in the treatment of a number of clinical disorders such as dysfunctional uterine bleeding, endometriosis, endometrial carcinoma, benign breast disease, threatened miscarriage, pre-eclampsia, perimenopausal symptoms and luteal phase defect.

Progesterone is likewise used for luteal phase support in assisted reproductive techniques, also known as assisted conception. Unfortunately, not all women of reproductive age can become naturally pregnant. Many of said women turn to Assisted Reproductive Technology (ART) to achieve pregnancy. There are, at least, three main types of ART: in vitro fertilization (IVF), which involves extracting the eggs, fertilizing them in the laboratory, and transferring resulting embryos to the uterus through the cervix; gamete intrafallopian transfer (GIFT), which involves placing unfertilized eggs and sperm into the woman's fallopian tubes using a laparoscope through an abdominal incision; and zygote intra-fallopian transfer (ZIFT) involves extracting the eggs, fertilizing them in the laboratory, and using a laparoscope to place the fertilized egg(s) into a woman's fallopian tubes. Among ART procedures are also considered intracytoplasmic sperm injection (ICSI), an IVF technique where a single sperm is injected directly into an egg; and frozen embryo transfer (FET), where an embryo that has been frozen (cryopreserved) is thawed and then transferred to the uterus/fallopian tube of a woman.

For many women, in conjunction with ART, steps must be taken to prime the uterus for embryo implantation. There have been many tools developed to aid in this process, amongst which exogenous progesterone supplementation stands out.

Progesterone is often externally supplied during the luteal phase and sometimes even beyond the luteal phase, although progesterone supplementation continuing beyond proper transformation of the endometrium into secretory phase is not strictly necessary. The goal of progesterone supplementation is in most cases to assist a corpus luteum that may have become compromised in ART procedures and cannot provide sufficient amounts of progesterone to achieve endometrial transformation into the secretory phase.

Different progesterone preparations are known in the art.

Progesterone may be administered orally, however due to its rapid clearance by the liver (hepatic first-pass effect), its bioavailability in the circulation, and particularly in the uterus, is low, leading to considerable inefficacy of oral progesterone formulations. Furthermore, in order to achieve sufficient levels of intrauterine progesterone that ensure endometrial proliferation, an administration of high doses of oral progesterone is necessary, which inevitably leads to build-up of progesterone metabolites in the blood which can in turn produce unwanted side-effects.

Intra-muscular (IM) progesterone is widely used, and although high serum levels can be achieved with IM administration, progesterone delivered in such a way is subject to uterine metabolism before exerting its therapeutic effect (uterine first pass effect) and its efficacy is thus considerably reduced. Furthermore, IM administration requires daily injections and is painful, uncomfortable, and inconvenient for patients.

Vaginal administration of progesterone generally results in higher endometrial progesterone levels when compared to the above administration routes, and in lower serum levels when compared to IM-delivered progesterone, and may therefore provide more efficient treatments with reduced systemic side-effects. Different types of progesterone vaginal administration are known.

Vaginal progesterone gel is less painful and easier to use than IM progesterone, but also requires daily dosing, may be messy, and due to potential leakage, may not provide a full dose with every application.

The use of progesterone vaginal inserts for tablet delivery is also known but again requires administering high doses of progesterone at least once daily. Vaginal micronized progesterone capsules are also known but require multiple daily administration that can be cumbersome for patients and may lead to treatment discontinuation.

Another known type of vaginal formulation is intravaginal rings. Intravaginal rings are designed to provide continuous release of progesterone and thus generally do not require daily, or even frequent, application of the formulation (i.e. replacing the ring daily or frequently), offering improved patient comfort.

U.S. Pat. No. 5,869,081 discloses the use of vaginal rings containing progesterone to prepare the endometrium for embryo implantation in a series of women patients. Zegers-Hochschild et al. (Human Reproduction, 2000, 15(10), 2093-2097) further report the clinical use of one of such vaginal rings to successfully achieve pregnancy in a series of patients who suffered premature ovarian failure or lack of response to ovarian stimulation.

Stadtmauer et al. (Fertility and Sterility, 2013, 99(6), 1543-1549) similarly report that administration of a weekly progesterone vaginal ring is effective for luteal supplementation and progestational support as part of ART treatments for women with infertility.

International patent application WO 2009/099586 likewise reports the use of vaginal rings comprising progesterone along with a hydrocarbon or glycerol esters of a fatty acid for treating a luteal phase defect.

Clinical studies which employ progesterone rings for ensuring adequate endometrial proliferation, generally record vaginal bleeding in patients at some point throughout the treatment, particularly during the first weeks of said treatment. This is the case for the above mentioned vaginal rings. Bleeding is generally associated to low levels of intrauterine progesterone and is sometimes addressed during treatment by administering additional progesterone to the patient. However, increasing progesterone levels is not a particularly desirable solution due to possible side effects that can arise from build-up of progesterone or from metabolites therefrom. On the other hand, it should be taken into account that, even if it may not be a sign of pregnancy complication, bleeding always worries the patients and it can lead to an unnecessary medical consultation. Thus, it is always desirable to provide a treatment that avoids or minimizes bleeding during early pregnancy.

A constant need exists to develop new, alternative formulations which overcome the drawbacks of existing dosage forms of progesterone. In particular, it seems rather necessary to develop formulations which provide low plasma levels of progesterone whilst maintaining therapeutic efficacy, improving the safety/comfort profile for patients and minimizing bleeding during early pregnancy.

SUMMARY OF THE INVENTION

The present inventors unexpectedly found that vaginal devices comprising progesterone in polymorphic form I or progesterone displaying a high percentage of polymorphic form I are effective in transforming the endometrium into secretory phase whilst minimizing or not increasing the risk of vaginal bleeding. As a consequence, progesterone can be supplied to patients without the need to replace the device or to add another progesterone formulation during treatment (at least until endometrial transformation into secretory phase is reported). Preferably the vaginal devices of the invention comprise progesterone in low amounts providing low progesterone serum levels.

Therefore, the present invention is directed to an intravaginal device comprising progesterone, wherein at least 75% of said progesterone is in polymorphic form I.

Another aspect of the invention refers to a process for making a vaginal device according to the present invention, comprising the steps of:
a) Mixing progesterone, wherein at least 75% of the progesterone is in polymorphic form I, with a pharmaceutically acceptable polymeric composition.
b) Curing the mixture resulting from step a) at a temperature of 120° C. or lower.

The present inventors have also discovered that reducing the amount of progesterone in the devices of the invention to levels lower than those generally employed in devices of the previous art results in intravaginal devices which can be employed to successfully transform the endometrium into secretory phase and maintain pregnancy whilst minimizing, or even avoiding, vaginal bleeding in pregnant women.

Thus in a particular embodiment, the device of the invention comprises from 17.4% to 2.9% wt progesterone with respect to the total weight of the device, more preferably from 11.6% to 2.9% wt progesterone, even more preferably from 8.7% to 2.9% wt progesterone.

The present inventors have surprisingly found that vaginal devices prepared according to the process of the invention are stable during at least 3 years under normal (room temperature) and accelerated (up to 30° C.) storage conditions, exhibit significant lesser "blooming" (migration to the surface of the ring) of progesterone, contribute to a lesser "burst" effect (initial excessive release) of progesterone and show a slower release of progesterone in vitro.

A different aspect of the invention refers to the use of the intravaginal device of the invention in the treatment of infertility in a female subject.

Yet another aspect relates to the use of the intravaginal device of the invention in the treatment of symptoms of the perimenopause.

In a preferred embodiment of the invention, the device is an intravaginal ring.

DETAILED DESCRIPTION OF THE INVENTION

Figure 1:
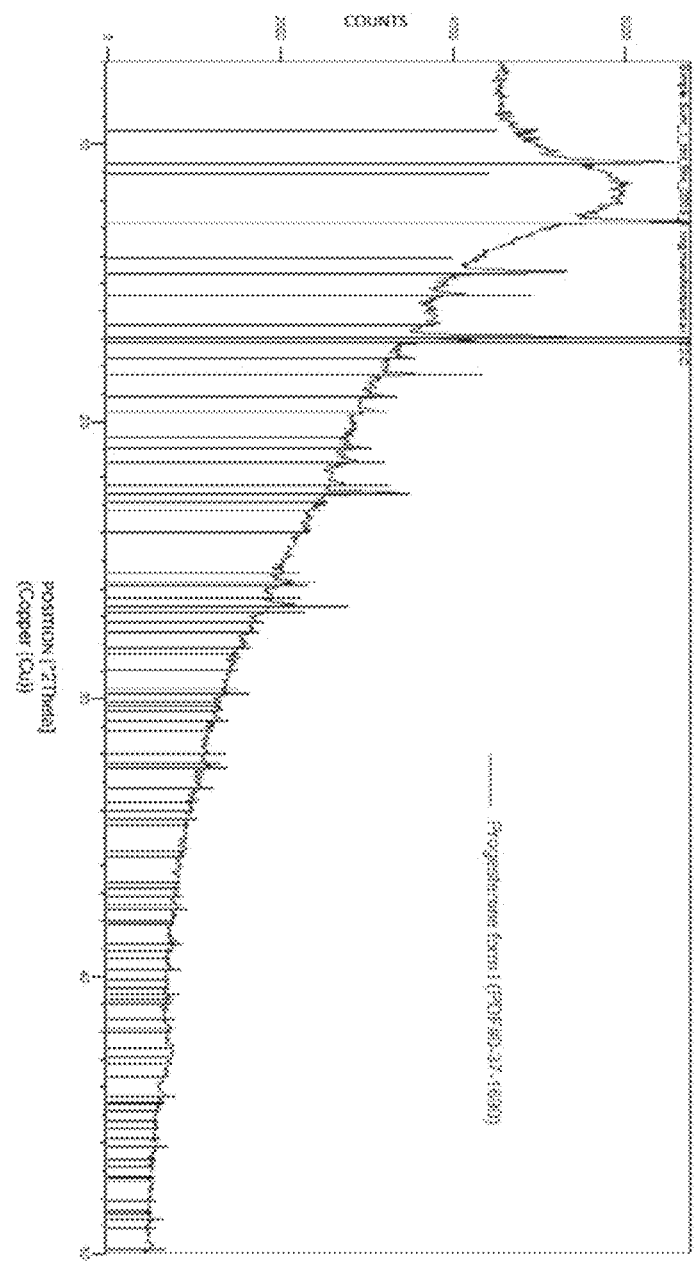
FIG. 1. X-ray diffractogram of a sample obtained from an intravaginal ring according to the present invention.

It is well established that organic compounds may exist in different crystalline forms known as polymorphs. Different polymorphs or polymorphic ratios of a particular substance can provide markedly different therapeutic behavior.

Progesterone is a poorly soluble drug in water that can present different polymorphic forms, out of which the most studied are two: form I (or alpha) and form II (or beta) (Araya-Sibaja et al., Scanning, 2013, 35(4), 213-221).

Progesterone in pure polymorphic form I, or in a polymorph-I enriched form may be prepared by methods known in the art (e.g. that described in Barrio et al., Journal of Pharmaceutical Sciences, 2009, 98(5), 1657-1670). Progesterone polymorphic form I forms characteristic prism-like crystals when crystalised from dilute alcohol (O'Neil et al., The Merck Index, 13th Ed., 2001, 7866). Different analytical techniques are employed in the art to detect and/or quantify progesterone polymorphic form I, namely differential scanning calorimetry (DSC), X-ray diffraction, Infrared Spectroscopy or Raman Spectroscopy (Wang et al., Organic Process Research & Development, 2000, 4, 391-395). The most typically employed technique is differential scanning calorimetry, by which progesterone polymorphic form I reveals a characteristic endotherm at about 128-130° C., corresponding to its melting point.

In the context of the present invention, progesterone is employed in its natural form, i.e. that produced by the ovaries. Nevertheless, pharmaceutical salts or solvates of progesterone are also within the scope of the invention. In particular, pharmaceutical salts or solvates of progesterone polymorphic form I are within the scope of the present invention.

Throughout the present disclosure, all expressions of percentage, ratio, and the like are "by weight" unless otherwise indicated. As used herein, "by weight" is synonymous with the term "by mass," and indicates that a ratio or percentage defined herein is done according to weight rather than volume, thickness, or some other measure.

As used herein, the term "about," when used in conjunction with a percentage or other numerical amount, means plus or minus 1% of that percentage or other numerical amount. For example, the term "about 80%," would encompass 80% plus or minus 0.8%.

Preferably, the intravaginal ring of the present invention is annular in shape. As used herein, "annular" refers to a shape of, relating to, or forming a ring. Annular shapes suitable for use with the present invention include a ring, an oval, an ellipse, a toroid, and the like. The shape of the intravaginal ring of the present invention can be altered or deformed temporarily, i.e., can temporarily assume a non-annular shape, e.g., when being inserted into the vagina. Ring diameter values below are given with respect to the rings of the invention in a non-deformed state.

In an embodiment of the invention, substantially all of the progesterone in the device is in polymorphic form I. The term "substantially all" as herein used means that the progesterone comprised in the intravaginal device contains at most about 5%, preferably about 2.5%, more preferably about 1.5% or less, preferably about 0.5% or less of other polymorphic forms, particularly polymorphic form II, or contains no detectable amounts of other polymorphic forms, particularly polymorphic form II.

At least about 75% of the progesterone comprised in the intravaginal device of the invention is in polymorphic form I. In another embodiment at least about 80% of the progesterone comprised in the intravaginal device is in polymorphic form I. In another embodiment at least about 85% of the progesterone comprised in the intravaginal device is in polymorphic form I. In another embodiment at least about 90% of the progesterone comprised in the intravaginal ring is in polymorphic form I. In a preferred embodiment at least about 95% of the progesterone comprised in the intravaginal device is in polymorphic form I.

In another embodiment from about 75 to about 96, 97, 98, 99 or 100% of the progesterone comprised in the intravaginal device is in polymorphic form I. In another embodiment from about 80 to about 96, 97, 98, 99 or 100% of the progesterone comprised in the intravaginal device is in polymorphic form I. In another embodiment from about 85 to about 96, 97, 98, 99 or 100% of the progesterone comprised in the intravaginal device is in polymorphic form I. In another embodiment from about 90 to about 96, 97, 98, 99 or 100% of the progesterone comprised in the intravaginal device is in polymorphic form I. In another embodiment from 95 about to about 96, 97, 98, 99 or 100% of the progesterone comprised in the intravaginal device is in polymorphic form I. In a preferred embodiment about 100% of the progesterone comprised in the intravaginal device is in polymorphic form I.

The present inventors have surprisingly found that an intravaginal device comprising progesterone, wherein at least 75% of said progesterone is in polymorphic form I, can be employed to successfully supplement said hormone in treatments for infertility, particularly those related to assisted reproductive techniques.

The present inventors have also unpredictably discovered that reducing the amount of progesterone in the devices of the invention to levels lower than those generally employed in devices of the previous art (with which vaginal bleeding can be observed during the progesterone supplementation period) still results in intravaginal devices which can be employed to successfully transform the endometrium into secretory phase and maintain pregnancy whilst minimizing, or even avoiding, vaginal bleeding in pregnant women.

In an embodiment of the invention or in any of the above embodiments, the intravaginal device comprises about 1.50 g progesterone or lower. In another embodiment it comprises about 0.75 g progesterone or lower. In another embodiment it comprises about 0.70 g progesterone or lower. In another embodiment it comprises about 0.50 g progesterone or lower. In another embodiment it comprises about 0.375 g progesterone or lower. In another embodiment it comprises about 0.125 g progesterone or lower. In another embodiment it comprises about 0.100 g progesterone.

In another embodiment it comprises from about 1.50 to about 0.100 g progesterone. In another embodiment it comprises from about 1.50 to about 0.125 g progesterone. In another embodiment it comprises from about 1.50 to about 0.25 g progesterone. In a preferred embodiment it comprises from about 1.5 to about 0.375 g progesterone.

In another embodiment it comprises from about 0.75 to about 0.100 g progesterone. In another embodiment it comprises from about 0.75 to about 0.125 g progesterone. In another embodiment it comprises from about 0.75 to about 0.25 g progesterone. In a preferred embodiment it comprises from about 0.75 to about 0.375 g progesterone.

In another embodiment it comprises from about 0.70 to about 0.100 g progesterone. In another embodiment it comprises from about 0.70 to about 0.125 g progesterone. In another embodiment it comprises from about 0.70 to about 0.25 g progesterone. In a preferred embodiment it comprises from about 0.70 to about 0.375 g progesterone.

In another embodiment it comprises from about 0.50 to about 0.100 g progesterone. In a preferred embodiment it comprises from about 0.50 to about 0.125 g progesterone. In a preferred embodiment it comprises from about 0.5 to about 0.25 g progesterone. In a more preferred embodiment it comprises from about 0.5 to about 0.375 g progesterone.

In a preferred embodiment it comprises from about 0.375 to about 0.100 g progesterone. In a more preferred embodiment it comprises from about 0.375 to about 0.125 g progesterone. In a preferred embodiment it comprises from about 0.375 to about 0.25 g progesterone.

In a particular embodiment it comprises about 1.50 g progesterone. In a particular embodiment it comprises about 0.75 g progesterone. In a particular embodiment it comprises about 0.70 g progesterone. In a particular embodiment it comprises about 0.50 g progesterone. In a preferred embodiment it comprises about 0.375 g progesterone. In a particular embodiment it comprises about 0.25 g progesterone. In a particular embodiment it comprises about 0.125 g progesterone.

In an embodiment of the invention, the intravaginal device comprises an amount of about 34.8% progesterone or lower with respect to the total weight of the ring. In another embodiment it comprises about 17.4% progesterone or lower. In another it comprises about 16.2% progesterone or lower. In a preferred embodiment it comprises about 11.6% progesterone or lower. In a more preferred embodiment it comprises about 8.7% progesterone or lower. In another embodiment it comprises about 2.9% progesterone In another embodiment it comprises from about 34.8% to about 2.9% progesterone. In another embodiment it comprises from about 34.8% to about 5.8% progesterone. In another embodiment it comprises from about 34.8% to about 8.7% progesterone.

In another embodiment it comprises from about 17.4% to about 2.9% progesterone. In another embodiment it comprises from about 17.4% to about 5.8% progesterone. In a preferred embodiment it comprises from about 17.4% to about 8.7% progesterone.

In another embodiment it comprises from about 16.2% to about 2.9% progesterone. In another embodiment it comprises from about 16.2% to about 5.8% progesterone. In a preferred embodiment it comprises from about 16.2% to about 8.7% progesterone.

In a preferred embodiment it comprises from about 11.6% to about 2.9% progesterone. In a preferred embodiment it comprises from about 11.6% to about 5.8% progesterone. In a more preferred embodiment it comprises from about 11.6% to about 8.7% progesterone.

In a more preferred embodiment it comprises from about 8.7% to about 2.9% progesterone. In a preferred embodiment it comprises from about 8.7% to about 5.8% progesterone.

In a particular embodiment it comprises about 34.8% progesterone. In a particular embodiment it comprises about 23.2% progesterone. In a particular embodiment it comprises about 17.4% progesterone. In a particular embodiment it comprises about 16.24% progesterone. In a preferred embodiment it comprises about 11.6% progesterone. In a more preferred embodiment it comprises about 8.7% progesterone. In a preferred embodiment it comprises about 5.8% progesterone. In a particular embodiment it comprises about 2.9% progesterone.

In particular embodiments, in any and each of the above mentioned specific percentage ranges or percentages and/or specific weight ranges or weights, at least about 95% of the progesterone comprised in the intravaginal device is in polymorphic form I. In a preferred embodiment, the intravaginal device comprises an amount of from about 34% to about 3% progesterone with respect to the total weight of the ring, and from about 90 to about 96, 97, 98, 99 or 100% of the progesterone comprised in the intravaginal ring is in polymorphic form I.

In another preferred embodiment, the intravaginal device comprises an amount from about 17% to 6% progesterone with the respect to the total weight of the device, and at least about 95% of the progesterone in the intravaginal device is in polymorphic form I.

In another preferred embodiment, the intravaginal device comprises an amount from about 12% to 7% progesterone with the respect to the total weight of the device, and at least about 99% of the progesterone in the intravaginal device is in polymorphic form I.

In another preferred embodiment, the intravaginal device comprises an amount of from about 9 to about 8% progesterone with respect to the total weight of the device, and about 100% of the progesterone comprised in the intravaginal device is in polymorphic form I.

The present inventors have surprisingly found that an intravaginal device of the invention, preferably in the form of a ring, comprising progesterone in amounts lower than 35% by weight, wherein at least 75% of said progesterone is in polymorphic form I, can be employed to successfully supplement said hormone in treatment for infertility, particularly those related to assisted reproductive technologies, during at least 14 days without the need to be replaced for another device containing progesterone in higher amounts nor the need to add other formulation of progesterone.

In an embodiment or in any of the previous embodiments, the device further comprises a pharmaceutically acceptable polymeric composition as pharmaceutically acceptable carrier. The pharmaceutically acceptable carrier as well as any other material used in the intravaginal device of the present invention is suitable for placement in the vaginal tract of a subject and is nontoxic to the subject. The materials are also suitable for being shaped into an intravaginal device, preferably a ring or similar forms.

Pharmaceutically acceptable polymeric compositions suitable for use in the intravaginal devices disclosed herein include, but are not limited to, olefin and vinyl-type polymers, carbohydrate-type polymers, condensation-type polymers, rubber-type polymers, and/or polysiloxanes. Other exemplary polymers that can be used include poly(ethylene-vinyl acetate), poly(methylacrylate), poly(butylmethacrylate), plasticized poly(vinylchloride), plasticized nylon, plasticized poly(ethylene terephthalate), poly(ethylene), poly(acrylonitrile), poly(trifluorochloroethylene), poly(4,4'-isopropylene-diphenylene carbonate), poly(ethylenevinyl esters), poly(vinyl chloridediethyl fumarate), poly(esters of acrylate and methacrylate), cellulose acetate, cellulose acylates, partially hydrolyzed poly(vinyl acetate), poly(vinyl butyral), poly(amides), poly(vinyl carbonate), poly(urethane), poly(olefins), poly(styrene), poly(styrene-butadiene) and combinations thereof. These polymers and their physical properties as well as methods of synthesis are known in the art.

In particular embodiments, the pharmaceutically acceptable polymeric composition comprises at least one elastomer.

The term "elastomer" is that understood by the skilled artisan. In particular, it refers to an amorphous polymer network formed when a polymer or a mixture of polymers undergo cross-linking. Each polymer is comprised of monomeric units, which are linked together to form the polymer. The monomeric units comprise carbon, hydrogen, oxygen, silicon, halogen, or a combination thereof. Elastomers can be easily bent, stretched, twisted, or deformed and, when released, quickly return to their approximate original dimensions and shape. Elastomers provide the intravaginal devices with sufficient structural integrity for ensuring therapeutic use and sufficient flexibility to adapt to the body of the patient and provide maximum patient comfort.

Preferably, the pharmaceutically acceptable polymeric composition comprises at least one silicone-based elastomer, e.g. a polysiloxane. As used herein, a "polysiloxane" refers to any of various compounds containing alternate silicon and oxygen atoms in either a linear or cyclic arrangement. In particular embodiments, the polysiloxane is a diorganopolysiloxane, such as diarylpolysiloxanes and dialkylpolysiloxanes. In a particular embodiment, the polysiloxane is vinyl dimethyl-endblocked. In a more particular embodiment, the polysiloxane is vinyl-endblocked dimethylpolysiloxane.

In other embodiments, the pharmaceutically acceptable carrier comprises at least one non-silicone elastomer, e.g. a styrene copolymer such as poly(styrene-butadiene).

In a preferred embodiment, the intravaginal device of the invention does not comprise other materials in addition to progesterone and the pharmaceutically acceptable polymeric composition. However, in a different embodiment, the intravaginal device of the invention may comprise other materials in addition to progesterone and the pharmaceutically acceptable polymeric composition.

In a preferred embodiment, the intravaginal device of the invention does not comprise other materials in addition to progesterone, the pharmaceutically acceptable polymeric composition, and any substance or substance derived from the substance or substances necessary for the preparation of the device and which forms part of the device after its preparation, such as any of those mentioned herein, e.g. cross-linking catalysts or catalyst inhibitors.

In a preferred embodiment, the intravaginal device of the invention does not comprise a pharmaceutically acceptable excipient in addition to progesterone and the pharmaceutically acceptable polymeric composition. However, in a different embodiment, the intravaginal device of the invention may comprise a pharmaceutically acceptable excipient in addition to progesterone and the pharmaceutically acceptable polymeric composition. Non-limiting examples of pharmaceutically acceptable excipients for vaginal use include wetting agents, surfactants, polaxomers, carbomers, polyvinyl alcohol, silicon dioxide, sodium carboxymethyl cellulose, emulsifiers, nonionic surfactants, Tween, Tween 80, polysorbate 80, a-lipoic acid, a-tocopherol, ascorbyl palmitate, benzyl alcohol, biotin, bisulfites, boron, butylated hydroxyanisole, butylated hydroxytoluene, ascorbic acid, carotenoids, calcium citrate, acetyl-L-carnitine, chelating agents, chondroitin, chromium, citric acid, coenzyme Q-10, cysteine, cysteine hydrochloride, 3-dehydroshikimic acid, EDTA, ferrous sulfate, folic acid, fumaric acid, alkyl gallates, garlic, glucosamine, grape seed extract, gugul, magnesium, malic acid, metabisulfite, N-acetyl cysteine, niacin, nicotinomide, nettle root, ornithine, propyl gallate, pycnogenol, saw palmetto, selenium, sodium bisulfite, sodium metabisulfite, sodium sulfite, potassium sulfite, tartaric acid, thiosulfates, thioglycerol, thiosorbitol, tocopherol, tocopherol acetate, tocopherol succinate, tocotrienal, d-alpha-tocopherol acetate, vitamin A, vitamin B, vitamin C, vitamin D, vitamin E, zinc, carbohydrates, hydrocarbon or glycerol esters of a fatty acid or combinations thereof.

In a preferred embodiment, the intravaginal device of the invention does not comprise other active pharmaceutical ingredients in addition to progesterone. However, in a different embodiment, the intravaginal device of the invention may comprise other active pharmaceutical ingredients in addition to progesterone. In a particular embodiment, the other active pharmaceutical ingredient is a substance useful for enabling ovulation, embryo implantation and/or sustainment of early pregnancy. In a particular embodiment, the other active pharmaceutical ingredient is estrogen.

In another preferred embodiment, the intravaginal device of the invention does not comprise a pharmaceutically acceptable excipient nor other active pharmaceutical ingredients in addition to progesterone and the pharmaceutically acceptable polymeric composition, an optionally any substance or substance derived from the substances necessary for the preparation of the device and which forms part of the device after its preparation.

In embodiments comprising a pharmaceutically acceptable carrier, any of the above specified progesterone weight percentages or percentage ranges with respect to the weight of the device refer instead to the weight of progesterone with respect to the combined weight of progesterone and the pharmaceutical carrier.

Any of the above specific weights or weight ranges and weight percentages or percentage ranges may be individually combined to arrive at new embodiments. In a preferred embodiment, 0.375 g progesterone corresponds to about 8.7% progesterone with respect to the total weight of the ring or with respect to the combined weight of progesterone and the pharmaceutical carrier, and other specific weights as described above correspond to a weight percentage based on this ratio.

In an embodiment or in any of the above embodiments, progesterone is substantially homogeneously dispersed in the intravaginal device.

In an embodiment or in any of the above embodiments, the progesterone can be micronised. As used herein, "micronised" refers to particles of a composition that have been reduced to micron size. In a preferred embodiment or in any of the above preferred embodiments, the progesterone is not micronised. Advantageously, the use of non-micronised progesterone can prevent a "burst" effect by which progesterone is initially released in excess from the vaginal ring.

In an embodiment or in any of the above embodiments, the intravaginal device is in the form of a ring or a form approximately similar to a ring. Preferably the ring has an outer diameter of about 40 to about 65 mm. In another embodiment it has an outer diameter of about 50 to about 60 mm. In a preferred embodiment, the intravaginal ring has an outer diameter of about 58 mm. As used herein, an "outer diameter" refers to any straight line segment that passes through the center of the ring and whose endpoints are on the outer perimeter of the ring. Where the outer diameter of the ring is not constant along the entire perimeter, the outer diameter refers to the longest straight line segment that passes through the center of the ring and whose endpoints are on the outer perimeter of the ring.

In an embodiment or in any of the above embodiments, the intravaginal device, preferably ring, has a cross-sectional diameter of about 4 to about 10 mm. In another embodiment it has a cross-sectional diameter of about 5 to about 8 mm. In a preferred embodiment, the intravaginal ring has a cross-sectional diameter of about 5.5 mm. As used herein, a "cross-sectional diameter" refers to any straight line segment whose endpoints are on the inner and outer perimeter of the ring.

In a particular embodiment, the intravaginal ring has an outer diameter of about 50 to about 60 mm and a cross-sectional diameter of about 5 to about 8 mm. In a preferred embodiment, the intravaginal ring has an outer diameter of about 58 mm and a cross-sectional diameter of about 5.5 mm.

In an embodiment, the intravaginal device releases (in vivo) no more than or about 10 mg progesterone/day for at least 7 days. In another embodiment, the intravaginal ring releases (in vivo) no more than or about 10 mg progesterone/day for at least 14 days, preferably for a period between 14 and 18 days, more preferably for 14 days. In an embodiment, the intravaginal device releases (in vivo) between 4 and 8 mg progesterone/day for at least 7 days. In a preferred embodiment, the intravaginal device releases (in vivo) between 4 and 8 mg progesterone/day for at least 14 days, preferably for a period between 14 and 18 days, more preferably for 14 days. In a more preferred embodiment, the intravaginal device releases (in vivo) about 6 mg progesterone/day for at least 14 days, preferably for a period between 14 and 18 days, more preferably for 14 days. The release rate is measured by subtracting the remaining amount of progesterone in the device at the end of the treatment (e.g. day 14) to the amount of progesterone in the device at the beginning (day 0) and dividing the result by the number of days of treatment (e.g. 14).

In an embodiment, the intravaginal device allows reaching an average serum level of progesterone between 1-4 ng/ml for at least 7 days. In an embodiment, the intravaginal device allows reaching an average serum level of progesterone between 1-4 ng/ml for at least 14 days, preferably for a period between 14 and 18 days, more preferably 14 days. In a particular embodiment, the intravaginal device allows reaching a serum level of progesterone between 1.5-3.5 ng/ml for at least 14 days, preferably for a period between 14 and 18 days, more preferably 14 days. In a more particular embodiment, the intravaginal device allows reaching a serum level of progesterone about 2-3 ng/ml for at least 14 days, preferably for a period between 14 and 18 days, more preferably 14 days. 2-3 ng/ml of progesterone correspond to about 6.3-9.5 nmol/ml of progesterone.

In an embodiment, the serum levels of progesterone provided by the vaginal device or ring of the invention are approximately constant over the period of use of said ring, excluding the first 24 hours of use, during which serum levels build up. In particular embodiments, the period of use is at least 14 days, preferably is a period between 14 and 18 days, more preferably 14 days. "Constant" means that serum levels of progesterone are maintained at between about 3 and 14 nmol/L, more specifically at between about 6 and about 14 nmol/L, preferably at between about 6 and 12 nmol/L.

In another preferred embodiment, the intravaginal device or ring comprises between about 1.50 g and about 0.125 g progesterone, which corresponds to between about 34.8% and about 2.9% progesterone with respect to the total weight of the device, or with respect to the combined weight of progesterone and the pharmaceutical carrier, and provides constant serum levels of between about 3 and 14 nmol/L (excluding the first 24 hours of use, during which serum levels build up) during a period of use between 7 and 18 days, preferably of about 14 days, more preferably 14 days.

In a particularly preferred embodiment, the intravaginal device comprises between about 0.75 and 0.125 g progesterone, which corresponds to between about 17.4 and 2.9% progesterone with respect to the total weight of the device, or with respect to the combined weight of progesterone and the pharmaceutical carrier, and provides constant serum levels of between about 3 and 12 nmol/L (excluding the first 24 hours of use, during which serum levels build up) during a period of use between 7 and 18 days, preferably of about 14 days, more preferably 14 days.

In a particularly preferred embodiment, the intravaginal device comprises about 0.375 g progesterone, which corresponds to about 8.7% progesterone with respect to the total weight of the device, or with respect to the combined weight of progesterone and the pharmaceutical carrier, and provides constant serum levels of between about 6 and 12 nmol/L (excluding the first 24 hours of use, during which serum levels build up) during a period of use between 7 and 18 days, preferably of about 14 days, more preferably 14 days.

In another particular embodiment, the intravaginal device comprises from about 0.75 to about 0.25 g progesterone, which corresponds to from about 17.4% to about 5.8% progesterone with respect to the combined weight of progesterone and the pharmaceutical carrier, or with respect to the total weight of the device, and provides constant serum levels of between 1.5-3.5 ng/ml (excluding the first 24 hours of use, during which serum levels build up) during a period of use between 7 and 18 days, preferably of about 14 days, more preferably 14 days.

In sum, the present inventors have surprisingly found that an intravaginal device of the invention, preferably in the form of a ring, comprising progesterone in amounts lower than 35% by weight, wherein at least 75% of said progesterone is in polymorphic form I, can be employed to successfully supplement said hormone in treatment regimens for infertility, particularly those related to assisted reproductive technologies, during at least 14 days without the need to be replaced for another device containing progesterone in higher amounts nor the need to add other formulations of progesterone. Furthermore, the inventors have demonstrated that the use of such intravaginal device, even providing serum progesterone levels lower than or equal to 10 mg/day, unexpectedly avoids or minimizes vaginal bleeding during the progesterone supplementation period.

Figure 3:
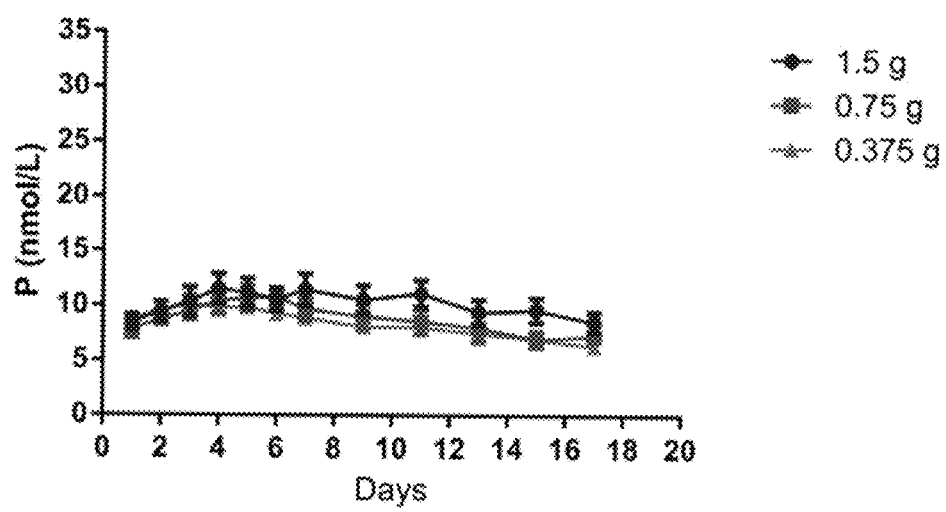
FIGS. 3 and 4. Plasma serum levels after administration of vaginal rings of the invention.
Figure 4:
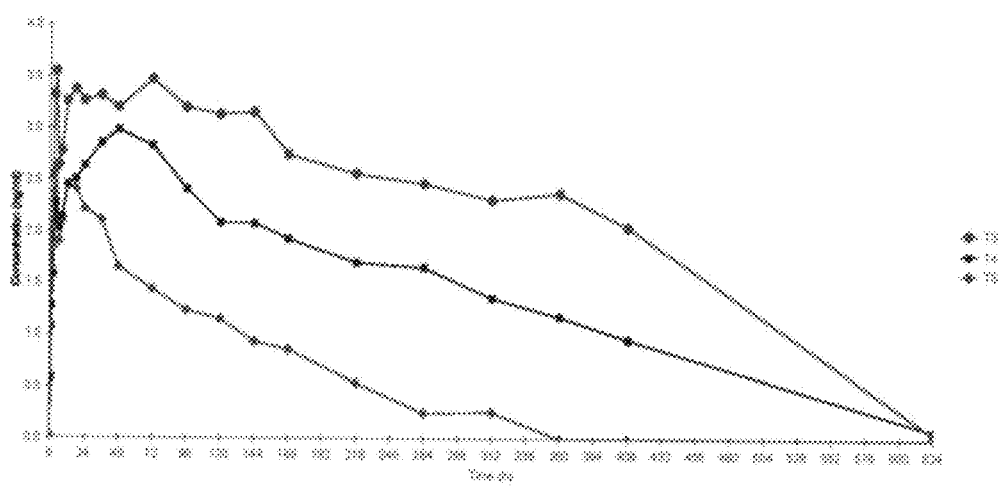

FIGS. 3 and 4 depict serum progesterone concentrations observed for vaginal rings according to the present invention, specifically intravaginal rings that comprise from about 0.125 g progesterone to about 1.50 g progesterone.

As mentioned above, the present invention also refers to a process for making a vaginal device or ring as described above, the process comprising the steps of:
a) Mixing progesterone, wherein at least 75% of the progesterone is in polymorphic form I, with a pharmaceutically acceptable polymer-forming composition; and then
b) Curing the mixture resulting from step a) at a temperature of 120° C. or lower.

The melting point of polymorphic form I of progesterone is generally reported to be 128-130° C. If subjected to temperatures higher to its melting point, progesterone turns into a metastable melt and the polymorphic form is lost (Barrio et al., Journal of Pharmaceutical Sciences, 2009, 98(5), 1657-1670). Thus, by curing the mixture resulting from step a) at 120° C., the percentage of progesterone in polymorphic form I in the device is maintained with respect to the starting material; that is, the loss of polymorphic form I is minimized.

Progesterone wherein at least 75% of it is in polymorphic form I can be obtained by methods known in the art, for instance that described by Barrio et al. Progesterone in substantially pure polymorphic form I can also be commercially obtained.

In an embodiment of the invention, substantially all of the progesterone in step a) is in polymorphic form I. In another embodiment, at least about 75% of the progesterone in step a) is in polymorphic form I. In another embodiment at least about 80% of the progesterone in step a) is in polymorphic form I. In another embodiment at least about 85% of the progesterone in step a) is in polymorphic form I. In another embodiment at least about 90% of the progesterone in step a) is in polymorphic form I. In another embodiment at least about 95% of the progesterone in step a) is in polymorphic form I.

In another embodiment from about 75 to about 100% of the progesterone in step a) is in polymorphic form I. In another embodiment from about 80 to about 100% of the progesterone in step a) is in polymorphic form I. In another embodiment from about 85 to about 100% of the progesterone in step a) is in polymorphic form I. In another embodiment from about 90 to about 100% of the progesterone in step a) is in polymorphic form I.

In a preferred embodiment, the purity in polymorphic form I in step a) corresponds to the purity in polymorphic form I in any of the above described intravaginal device and ring embodiments. As already mentioned, the process of the invention prevents the loss of polymorph I polymorphic purity in the vaginal device with respect to the progesterone starting material employed in step a).

Likewise, the weight of progesterone employed or the weight percentage of progesterone employed can be any of those described for the vaginal device embodiments above.

The present inventors have found that the presence of progesterone in polymorphic form I (in the weight percentages described in the above vaginal device embodiments) in the mixture resulting from step a) does not inhibit the curing of the polymeric composition in step b).

In a particular embodiment or in any of the above process embodiments, the curing of step b) is carried out in a mold. In a preferred embodiment, the process of the invention involves injection molding of the mixture resulting from step a) into the mold of step b). In a particular embodiment, the mold defines a cavity suitable for making intravaginal rings with the dimensions as described above.

Moreover, the present inventors have unexpectedly noticed that the resulting vaginal devices or rings, comprising at least 75% of the progesterone in polymorphic form I, may have the following advantageous properties, in comparison with devices or rings comprising less progesterone in polymorphic form I:

Significant lesser "blooming" (migration to the surface of the ring) of progesterone;

Lesser "burst" effect (initial excessive release) of progesterone;

Slower release of progesterone.

In a preferred embodiment, the curing of step b) can be carried out in very short periods of time when employing an elastomer-forming composition as described below as the pharmaceutically acceptable polymer-forming composition. Advantageously, the possibility of carrying out step b) in such short times provides for a process of making the progesterone vaginal device of the invention which is particularly well suited for industrial application.

Thus, in a particular embodiment or in any of the above process embodiments, step b) is carried out in a time of about 10 minutes or less, in a time of about 5 minutes or less, in a time of about 3 minutes or less, in a time of about 45 seconds or less, in a time of about 30 seconds or less. In a particular embodiment, step b) is carried out, in a time of about 10 minutes to about 15 seconds, in a time of about 5 minutes to about 30 seconds, in a time of about 3 minutes, in a time of about 2 minutes, in a time of about 90 seconds, in a time of about 1 minute, in a time of about 45 seconds, in a time of about 30 seconds. Preferably, step b) is carried out in a time between about 3 minutes and about 45 seconds.

In a particular embodiment or in any of the above process embodiments, the pharmaceutically acceptable polymer-forming composition is any polymer-forming material that crosslinks at a temperature lower than or equal to 120° C., preferably in 10 minutes or less, to form a pharmaceutically acceptable polymeric composition as described in any of the above embodiments.

In a particular embodiment or in any of the above process embodiments, the pharmaceutically acceptable polymer-forming composition is an elastomer-forming composition. In a particular embodiment, the elastomer-forming composition comprises at least one polysiloxane, preferably at least one diorganopolysiloxane, preferably dimethylpolysiloxane, any of which may be crosslinked to an elastomer. Preferably, the polysiloxane comprises per molecule at least two silicone-bonded groups having aliphatic unsaturation, e.g. a vinyl-endblocked polysiloxane. In a preferred embodiment, the polysiloxane is vinyl-endblocked. Preferably, the polysiloxane is vinyl dimethyl-endblocked. Preferably, the polysiloxane is vinyl-endblocked dimethylpolysiloxane. In other embodiments, the elastomer-forming composition comprises a non-silicone-based polymeric material such as poly(styrene-butadiene).

In a particular embodiment or in any of the above process embodiments, where applicable, the elastomer-forming composition comprises a crosslinking agent, which may be, for example, an H or OH, preferably H, endblocked polysiloxane, preferably an H or OH, preferably H, endblocked diorganopolysiloxane. In a particular embodiment, the polysiloxane is hydride dimethyl endblocked. In a more particular embodiment, the crosslinking agent is H-endblocked dimethylpolysiloxane.

In a particular embodiment or in any of the above process embodiments, where applicable, the elastomer-forming composition comprises a crosslinking catalyst which may be an organic metal compound, for example stannous octoate, dibutyltin dilaurate, alkyl titanates and titanium chelates, or a platinum complex. In a preferred embodiment, the crosslinking catalyst is a platinum complex, in particular which promotes the reaction between unsaturated groups (e.g. those of the above mentioned vinyl endblock) and silicon-bonded hydrogen groups (e.g. those of the above mentioned H-endblock), for example chloroplatinic acid, platinum acetylacetonate, a complex of platinous halides with unsaturated compounds such as ethylene, propylene, organovinylsiloxanes and styrene, methyldiplatinum and $Pt(CN)_3$. Preferably the platinum complex is platinum complex in vinyl dimer.

In a particular embodiment or in any of the above process embodiments, where applicable, the elastomer-forming composition comprises a catalyst inhibitor, for example an alkynyl compound such as an acetylenically unsaturated secondary or tertiary alcohol for example ethynyl cyclohexanol. The aliphatically unsaturated groups are preferably olefinically unsaturated.

In a particular embodiment or in any of the above process embodiments, where applicable, the elastomer-forming composition comprises a silica filler such as treated silica.

Particularly preferred from an industrial point of view are elastomer-forming compositions which crosslink at a temperature of 120° C. or lower and in a time of about 10 minutes or less, such as elastomer-forming compositions comprising a vinyl dimethyl endblocked polysiloxane, a hydride dimethyl endblocked polysiloxane, a platinum-complex catalyst which promotes hydrosililation and a catalyst inhibitor. In a particular embodiment, the elastomer-forming composition comprises vinyl dimethyl endblocked polysiloxane, hydride dimethyl endblocked polysiloxane, platinum complex in vinyl dimer and ethynyl cyclohexanol. In a particular embodiment the elastomer-forming composition is DDR-4320 or DDU-4320 (commercially available from NuSil Technology LLC). In another particular embodiment the elastomer-forming composition is LSR92 or LSR86 (available from Bluestar/Elkem). In another particular embodiment, the elastomer-forming composition is Silbione Biomaterial LSR D140 (available from Bluestar/Elkem).

If the device, preferably ring, is to comprise one or more additional pharmaceutically acceptable excipients, depending on the nature of each pharmaceutically acceptable excipient, each pharmaceutically acceptable excipient will be added either during step a), during step b), or after step b). The skilled artisan understands when and how any excipient can be added. In the most preferred embodiment the ring does not comprise a pharmaceutically acceptable excipient other than the elastomer.

In a preferred embodiment of the process of the invention, step a) comprises:
  a1) Mixing progesterone with a pharmaceutically acceptable polymer-forming composition and a crosslinking catalyst to form mixture A; and
  a2) Mixing progesterone with a pharmaceutically acceptable polymer-forming composition and a crosslinking agent and a catalyst inhibitor to form mixture B;
  a3) Mixing mixtures A and B,
  wherein the pharmaceutically acceptable polymer-forming composition, the crosslinking catalyst, the crosslinking agent and the catalyst inhibitor are those described in any of the above process embodiments.

The concentration of progesterone in mixture A can be the same as that in mixture B or it can be different, so long as the final concentration is that described for any of the vaginal device embodiments above. In a particular embodiment, the concentration of progesterone in mixture A is the same as that in mixture B. The polymorph I polymorphic purity of the progesterone in mixture A can be the same as that in mixture B or it can be different, so long as the final polymorph I polymorphic purity is that described for any of the vaginal ring embodiments above. In a particular embodiment, the polymorph I polymorphic purity of progesterone in mixture A is the same as that in mixture B.

In an embodiment, when silica filler is employed, it forms part of mixture A.

In a particular embodiment, the mixing of step a3) implies adding mixture A and mixture B into a high speed mixer and mixing. In a more particular embodiment, the addition of mixture A and mixture B into the high speed mixer is at an approximately 1:1 ratio. In a particular embodiment, said addition is by pumping of the mixtures into the mixer. In a particular embodiment, the high speed mixer is a static in-line mixer. In a particular embodiment, the mixing of mixtures A and B is carried out by turbulence.

In an additional aspect, the present invention provides a vaginal device, preferably a ring, obtainable by any of the above mentioned process embodiments.

The present invention additionally refers to an intravaginal devices, preferably rings, as described in any of the embodiments above comprising
  a therapeutically effective amount of progesterone;
  a pharmaceutically acceptable carrier; for use in medicine.

The present invention also provides an intravaginal devices, preferably rings, as described in any of the embodiments above comprising
  a therapeutically effective amount of progesterone;
  a pharmaceutically acceptable carrier; for use in the treatment of infertility, particularly in assisted reproductive technology.

The present invention also provides an intravaginal devices, preferably rings, as described in any of the embodiments above comprising
  a therapeutically effective amount of progesterone;
  a pharmaceutically acceptable carrier; for use in the treatment of symptoms of the perimenopause.

In the context of the present invention, the treated subject is a female subject. In a particular embodiment, the female subject is a non-human female subject. In another embodiment the female subject is an animal. In another embodiment, the female subject is a human.

The present invention is also directed to a method for treating infertility, particularly assisted reproductive technology, in a female subject in need thereof, the method comprising administering to a patient an intravaginal device, preferably ring, as described in any of the embodiments above comprising
  a therapeutically effective amount of progesterone;
  a pharmaceutically acceptable carrier.

The present invention is also directed to a method for the treatment of symptoms of the perimenopause in a female subject in need thereof, the method comprising administering to a patient an intravaginal device, preferably ring, as described in any of the embodiments above comprising
  a therapeutically effective amount of progesterone;
  a pharmaceutically acceptable carrier.

The present invention is also directed to a method for the manufacture of an intravaginal device, preferably ring, as described in any of the embodiments above for the treatment of infertility, particularly in assisted reproductive technology, wherein the intravaginal device comprises
  a therapeutically effective amount of progesterone;
  a pharmaceutically acceptable carrier.

The present invention is also directed to a method for the manufacture of an intravaginal device, preferably ring, as described in any of the embodiments above for the treatment of symptoms of the perimenopause in a female subject, wherein the intravaginal device comprises
  a therapeutically effective amount of progesterone;
  a pharmaceutically acceptable carrier.

In the context of the present invention, the term "therapeutically effective amount" refers to an amount of progesterone in the vaginal device that allows achieving intrauterine progesterone levels sufficient to exert an adequate progestational effect in the endometrium for establishment and maintenance of early pregnancy. Concerning the treatment of symptoms of the perimenopause, the term "therapeutically effective amount" refers to an amount of progesterone in the vaginal device that successfully allows treating or alleviating a perimenopause symptom.

As used herein, unless otherwise indicated, the expressions "treating infertility", "treatment of infertiliy" and similar mean reversing or preventing the natural or induced inability of a female subject to establish embryo implantation and sustain early pregnancy, particularly refer to supporting luteal phase in assisted reproductive technologies, also called assisted conception. The terms also refer to alleviating, inhibiting the progress of, reversing or preventing symptoms of the perimenopause.

Luteal Phase Support in Infertility Treatments

The luteal phase is defined as the period from occurrence of ovulation until the establishment of a pregnancy or the resumption of menses 2 weeks later. In the context of assisted reproduction techniques, luteal phase support (LPS) is the term used to describe the administration of medications with the aim to support the process of implantation.

It is well established that luteal function is compromised in IVF cycles. The reasons for luteal phase abnormalities in ART are multiple. It has been shown that the function of the corpus luteum is compromised by the process of follicular aspiration for oocyte retrieval as granulosa cells are mechanically disrupted and aspirated. It has been proved that luteal phase defect occurs in long GnRh-agonist protocol and that corpus luteum deficiency as sequel of assisted reproduction techniques in general, is partially caused by the process of follicular aspiration for oocyte retrieval and the use of fertility medication for ovulation induction or follicle development stimulation, particularly gonadotropin-releasing hormone agonists. In the absence of luteal phase support, the area under the curve for progesterone was suboptimal and this was accompanied by premature luteolysis. In non-supported cycles, the length of the luteal phase was shortened and early bleeding occurred. Many meta-analyses concurred that luteal support improves IVF outcome. Luteal phase support with progesterone, compared to placebo or no treatment in GnRH agonist and non-GnRH agonist cycles, also resulted in a significant increase in clinical pregnancy rates and live birth.

As a consequence, luteal phase support, particularly by progesterone supplementation, is considered essential and in some cases mandatory to counter any luteal insufficiency that may arise during infertility treatments. Particularly, it has been proved that luteal phase support with progesterone improves pregnancy outcomes in anovulatory patients undergoing ovulation induction therapy, and in ovulatory patients undergoing stimulation of multiple follicle development prior to ARTs such as IVF, or prior to other infertility treatments such as intra-uterine insemination (IUI).

Thus, in a preferred embodiment of the present invention, the use of an intravaginal device, preferably a ring, as described in any of the embodiments above is for luteal phase support. In the context of the present invention, luteal phase support refers to the supplementation or substitution of progesterone to the female subject for helping or improving embryo implantation and early pregnancy sustainment.

In a preferred embodiment, in any of the above embodiments, the use of the intravaginal device of the present invention is in a female subject undergoing an infertility-treatment protocol. In a particular embodiment, the infertility-treatment protocol comprises administration of fertility medication. In a particular embodiment, the infertility-treatment protocol comprises ovulation induction or multiple follicular development stimulation. In a particular embodiment, the fertility medication is employed for ovulation induction or multiple follicular development stimulation.

In a particular embodiment, the infertility-treatment protocol is an ART protocol. In an even more particular embodiment, the ART protocol is IVF, ICSI, GIFT, ZIFT or FET. In a preferred embodiment the ART protocol is IVF or ICSI. In a particular embodiment the ART protocol is IVF. In a particular embodiment ART protocol is ICSI.

In another particular embodiment, the infertility-treatment protocol is an artificial insemination protocol. In a more particular embodiment, the artificial insemination protocol is IUI. It should be noted that "protocol" is employed in the present invention synonymously to "cycle", or the like.

In a particular embodiment, the female subject is anovulatory. In a particular embodiment, the female subject is anovulatory and is subjected to ovulation induction. In another particular embodiment, the female subject is ovulatory. In another particular embodiment, the female subject is ovulatory and is subjected to multiple follicular development stimulation.

In another embodiment, irrespective of whether the female subject is undergoing or will undergo an infertility-treatment protocol, the female subject suffers a luteal phase defect (LPD). The term "luteal phase defect" (LPD) refers to a disruption in the normal female menstrual cycle. LPD is also known as luteal phase insufficiency, inadequacy, defect, or deficiency. It can result from abnormalities at the level of the hypothalamus/pituitary, the ovary, or the endometrium, whereby the female body does not produce enough of the hormone progesterone or is not fully responsive to natural levels of the hormone. This results in a delay in the development of the lining of the uterus (endometrium) during the luteal phase. LPDs can result in the inability to transform the endometrium into secretory phase, whereby the uterine lining begins to break down, bringing on menstrual bleeding and causing miscarriage. In a particular embodiment, the LPD is caused by abnormal folliculogenesis, inadequate luteinizing hormone surge, inadequate secretion of progesterone by the corpus luteum, primary ovarian failure, absent ovaries, premature ovarian failure, diminished ovarian reserve, gonadal dysgenesis, idiopathic ovarian failure, agonadal functionality.

As is clear from the foregoing, the vaginal device of the present invention is envisaged for use in female subjects that are naturally progesterone-deficient but are not subjected to an infertility-treatment protocol, in female subjects that are not naturally progesterone-deficient but become so or can become so as a consequence of the infertility-treatment protocol, or in female subjects that are naturally progesterone-deficient and are subjected to an infertility-treatment protocol.

In a particular embodiment, in any of the above embodiments, the use of the intravaginal device of the present invention reduces the risk of spontaneous abortion (miscarriage) in the first trimester of pregnancy. In another particular embodiment, the use of the intravaginal device of the present invention reduces the risk of spontaneous abortion in the first two months of pregnancy. In an even more particular embodiment, reduces the risk of spontaneous abortion in the first month of pregnancy.

In another embodiment, in any of the above embodiments, the treatment of infertility involves administration of at least one other active substance useful for enabling ovulation, embryo implantation and/or sustainment of early pregnancy. In a particular embodiment, the at least one other active substance is an estrogen, which may be administered by routes known in the art. In a particular embodiment, the at least one other active substance and progesterone are comprised in the vaginal device of the invention.

Vaginal devices according to the present invention are effective in providing luteal phase support whilst advantageously preventing or reducing the risk of vaginal bleeding. As used herein, the term "vaginal bleeding" or "bleeding" refers to any kind of blood discharge through the vagina. It can range from spotting (few drops of blood) to hemorrhaging (heavier flow of blood). Preferably, it refers to severe bleeding and hemorrhage.

Thus, in a preferred embodiment, in any of the above embodiments, the vaginal devices of the invention are useful in the treatment of infertility and simultaneously in the prevention or reduction of the risk of vaginal bleeding. In a particular embodiment, the vaginal devices of the present invention are employed to replace a luteal support treatment that has resulted in vaginal bleeding or in excessive vaginal bleeding.

In a particular embodiment, in any of the above embodiments, the intravaginal device is not replaced for a period of at least 7 days (counted from insertion of the vaginal device). In a preferred embodiment, the intravaginal device is not replaced for a period of 14 days. In a particular embodiment, the intravaginal device is not replaced for a period of 15 days, of 16 days, of 17 days or of 18 days.

The present inventors have found that a device, preferably a ring, according to the present invention may be used without being removed or replaced during these periods of time to successfully transform the endometrium into secretory phase without observing any bleeding in the patient. In a particular embodiment, the intravaginal device is administered one to seven days before embryo transfer, two to six days before embryo transfer, three to five days before embryo transfer, or four days before embryo transfer. In a particular embodiment it is administered one day before embryo transfer.

Perimenopause

As mentioned above, the present invention is also useful for treating symptoms of the perimenopause. In the context of the present invention, a progesterone deficiency underlies or contributes to the symptoms of the perimenopause.

Menopause is defined as the absence of menstrual periods for 12 consecutive months in a female subject. Physical changes in the female subject begin years before the final menstrual cycle. This transition phase is called perimenopause and can last up to six to ten years. It begins with changes in the length of time between periods and ends twelve months after the last menstrual period. During the perimenopausal period more eggs are recruited and stimulated during each menstrual cycle, leading to higher-than-normal estrogen levels and lower-than-normal progesterone levels.

The intravaginal devices of the present invention are useful for progesterone supplementation in the perimenopausal period. The device can be supplemented by other hormone administration, either progesterone or other hormones such as estrogens.

Examples of the symptoms of the perimenopause that can be treated with the vaginal devices of the present invention are menorrhagia, irregular periods, hot flushes, night sweats, urinary incontinence, osteoporosis, sleep disorder, mood swings, nervousness, anxiety, palpitations, loss of memory and/or concentration, loss of libido, fatigue, urogenital atrophy, atrophy of the breasts or cardiovascular disease. In a preferred embodiment, the symptom of the perimenopause is menorrhagia, osteoporosis, sleep disorder or cardiovascular disease.

EXAMPLES

The following examples are for the purpose of illustration of the invention only and are not intended in any way to limit the scope of the present invention. It will thus be readily apparent to one skilled in the art that varying substitutions and modifications may be made to the invention disclosed herein without departing from the scope and spirit of the invention.

Example 1

Intravaginal Ring Process of Manufacture and Characterization

DDR-4320 (commercially available from NuSil Technology LLC) is employed in the preparation of the vaginal rings of the invention. The composition of DDR-4320 is the following:

Part A—vinyl dimethyl endblock silicone polymer; platinum complex in vinyl dimer.
Part B—vinyl dimethyl endblock silicone polymer; hydride dimethyl endblock silicone polymer, ethynyl cyclohexanol.

1.9675 g Part A is mixed with 0.1875 g progesterone (wherein substantially all of the progesterone in the ring is in polymorphic form I; commercially obtained). In a separate vessel, 1.9675 g Part B is mixed with 0.1875 g progesterone (same progesterone as that employed for mixing with Part A).

The two mixtures are pumped in 1:1 proportion to a static in-line mixer where they are mixed by turbulence. This mixture is injected in a mold where the rings are formed by curing at 120° C. for 45 seconds. The intravaginal ring thus obtained weighs 4.31 g and is composed of the following:

| Name of Ingredient | Function | % (w/w ring) | Reference to standards |
|---|---|---|---|
| Progesterone | API | 8.7 | Ph. Eur. and USP |
| LSR DDR-4320. Part A | Vehicle | 45.65 | Internal method |
| LSR DDR-4320. Part B | Vehicle | 45.65 | Internal method |

Identification and Quantification of Intravaginal Ring Progesterone Polymorph I by X-Ray Diffraction
Instrument and Experimental Conditions The obtained ring was cut to get disc shape samples of about 1 millimeter of thickness. The disc shape samples were sandwiched between polyester films of 3.6 micrometers of thickness.

Samples were analysed with a PANalytical X'Pert PRO MPD θ/θ powder diffractometer of 240 millimetres of radius, in a configuration of convergent beam with a focalizing mirror and a transmission geometry with flat samples sandwiched between low absorbing films. The following conditions were employed:

Cu Kα radiation ($\lambda$=1.5418 Å).
Work power: 45 kV-40 mA.
Incident beam slits defining a beam height of 0.4 millimetres.
Incident and diffracted beam 0.02 radians Soller slits.
PIXcel detector: Active length=3.347°.
2θ/θ scans from 2 to 70° 2θ with a step size of 0.026° 2θ and a measuring time of 600 seconds per step.

Results

The observed crystalline peaks indicate the presence of the crystalline form I (alpha form) of progesterone, and no other polymorphs, particularly form II, were found. FIG. 1 depicts the X-ray powder diffractogram of the sample with the peaks corresponding to the reference pattern PDF #0-37-1690 of the progesterone form I (alpha form) superimposed (reference pattern depicted as vertical lines, analysed sample depicted as peaks). With this instrumental technique and the type of sample, the quantification limit is 1-5%. Therefore, it can be assured that the form I polymorphic purity is at least 95%.

By Differential Scanning Calorimetry
Instrument and Experimental Conditions

In the context of the present invention, polymorphic purity values are calculated based on enthalpy readings obtained by the DSC method that follows.

Samples prepared in an aluminium crucible with a capacity of 40 µL. Samples were analysed with a Mettler Toledo DSC822e. The following conditions were employed:

Gas: Dry nitrogen 50 mL/min.
Method: Heating from 30° C. to 200° C. at a rate of 10° C./min.

Results

Figure 2:
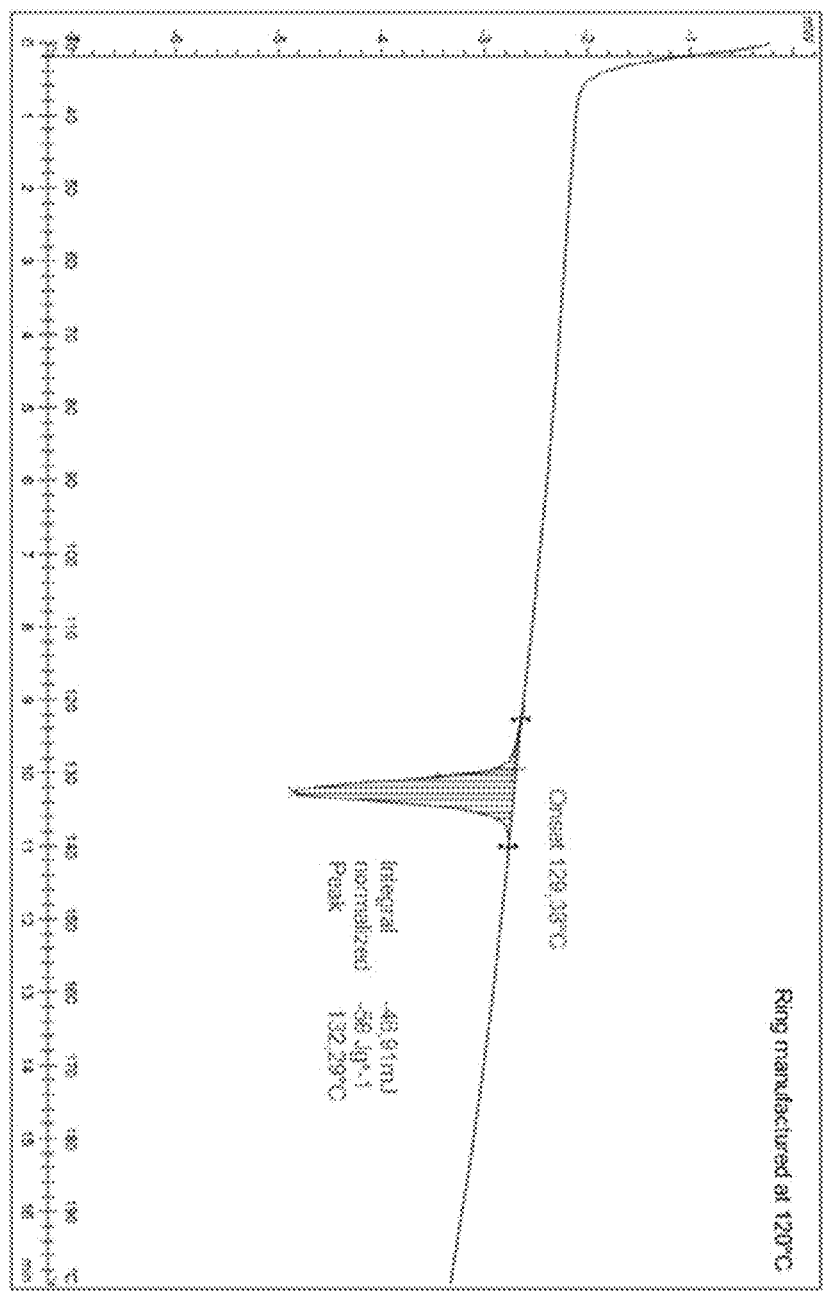
FIG. 2. Differential scanning calorimetry curve for a sample obtained from an intravaginal ring according to the present invention.

The obtained curve indicates the presence of the crystalline form I (alpha form) of progesterone, and that no other polymorphs, particularly form II, were found. FIG. 2 depicts the DSC curve which shows an endothermic phenomenon from 129° C. with an associated heat of 5.83 J/g. This endotherm can be attributed to the melting of polymorph form I (alpha form) of progesterone. No other characteristic endotherms were identified.

Example 2

A Pharmacokinetic, Pharmacodynamics and Tolerability Study to Evaluate Three Vaginal Rings Containing 0.375 g, 0.125 g and 0.040 g of Natural Progesterone in Healthy Premenopausal Female Volunteers This is a phase I-II single-center, randomized, active-controlled, parallel-group, dose-response clinical trial.
Objectives:
1. Evaluate the pharmacokinetic profile of three vaginal rings containing 0.375 g, 0.125 g and 0.040 g of progesterone, respectively
2. Evaluate the effect of the three vaginal rings in producing gestagenic transformation of the endometrium
3. Evaluate the tolerability and acceptability of the progesterone vaginal rings
Number of Subjects:
  24 subjects in total, 8 per test group
Medical Condition or Disease Under Investigation:
  Study population are healthy volunteers, although the test product is designed for the treatment of luteal phase deficiency (LPD) in the context of in vitro fertilization (IVF)/assisted reproduction techniques (ART).
Inclusion Criteria:
  Healthy adult woman of child-bearing potential (18-45 years inclusive).
  Body Mass Index (BMI) range limit of 18-25 kg/m2 (both inclusive).
  Normal vaginal aspect.
  Normal cervical cytology.
  Seronegativity for hepatitis B surface antigen (HBsAg), hepatitis C virus antibodies (AbHCV), human immunodeficiency virus (HIV).
  Written informed consent illustrating awareness and willingness to comply with the protocol procedures and assessments.
  Willingness to suspend oral contraceptives for the duration of the study period.
Exclusion Criteria:
  Relevant gynecological pathology (endometriosis, polycystic ovary syndrome (PCOS), uterine abnormalities that affect the endometrial cavity).
  Any recent or concomitant pathology that contraindicates or prohibits endometrial biopsy.
  Relevant vulvovaginitis (infectious or non-infectious) at any time in the month prior to enrolment.
  Any contraindication to the use of estrogens (neoplasm, etc.).
  Concomitant use of intrauterine device (IUD) and/or hormonal implants.
  Active smoker (if older than 35 years).
  Any concomitant illness that may in the opinion of the investigator jeopardize study-compliance.
  Hypersensitivity, allergy or known tolerance to the active ingredient or excipients of the medicines used in this study (leuprorelin acetate, estradiol hemihydrate, progesterone).
  Pregnancy, intention to become pregnant or lactation.
  Participation in another clinical study involving a new chemical entity within 3 months prior to enrolment in this study. (If involving generics within 4 weeks prior to enrolment in this study).
  Not willing and able to use a barrier-method contraception.
  Intact hymen.
  Venous thromboembolic disorders (deep vein thrombosis, pulmonary embolism) or arterial (angina, myocardial infarction, stroke).
  Coagulopathy or any disorder that could affect the subject's hypercoagulability state.
Study Treatment:
Test Products and Dose:
  T3: vaginal ring with 0.375 g of natural progesterone
  T4: vaginal ring with 0.125 g of natural progesterone
  T5: vaginal ring with 0.040 g of natural progesterone
Mode of administration: single insertion of one ring in each subject
Apart from the Study Treatment, each Subject Receives the Following Treatments:
  GnRH-a injections to suppress endogenous hormone production
  Estrogen patches to generate a proliferative phase of the endometrium
  Optionally, the subject may receive one cycle of oral contraception at the end of study
Duration of Treatment:
  18±1 days
Study Procedures and Assessments:
  Twenty visits have been scheduled, including screening visits, hospitalization in a phase I clinical unit for two nights, follow-up visits and a final telephone contact. Each subject's participation is organized into a screening/preparation phase of up to 5 weeks, a study treatment period of approximately 18 days, a follow-up period of approximately 10 days and a final observation period of 3 weeks: in total 9 weeks of study visits and 12 weeks in total of study participation.
Selection/Screening:
  Each subject comes to the clinical unit (CU) for an initial visit (visit 0) during which the study is explained in full details and formal consent requested. If consented, the subject undergoes a general medical examination and general lab test (clinical chemistry, hematology, serology, urinalysis) and cytology.
  Visit 1 includes gynecological examination, pregnancy test, a review of eligibility, vaginal echography, blood draw (to determine hormone levels) and a GnRH-a IM injection (Ginecrin Depot 3.75 mg).
  Visit 2 should take place once the subject's menstruation has finished and includes gynecological examination, confirmation of hormone suppression (by vaginal echography to confirm endometrial thickness less than 7 mm and blood draw to determine 17-β-estradiol less than 60 pg/ml). The subject then starts estrogen treatment (Estradot 75 mcg/d patches).
  Visit 3 includes a second and final GnRH-a IM injection (Ginecrin Depot 3.75 mg).
  Visit 4 includes a gynecological examination, vaginal echography to confirm endometrial thickness>7 mm, and blood draw to determine progesterone levels which must be less than 1 ng/ml.

Visit 5 is when the subject must be hospitalized in the CU for randomization, study drug treatment, and PK blood draws. Visits 6, 7 involve further PK sampling.

Visit 8 includes a gynecological examination, vaginal echography, and blood draw to determine hormone levels.

Visit 9, 10 include blood draw to determine hormone levels.

Visit 11 includes a gynecological examination, vaginal echography and blood draw to determine hormone levels.

Visit 12 includes a blood draw to determine hormone levels.

Visit 13 includes a gynecological examination, vaginal echography and blood draw to determine hormone levels.

Visit 14 includes a blood draw to determine hormone levels.

Visit 15 includes a gynecological examination, vaginal echography, blood draw to determine hormone levels and endometrial biopsy.

Visit 16 includes a blood draw to determine hormone levels.

Visit 17 includes a gynecological examination, vaginal echography and blood draw to determine hormone levels. Study treatment ends here with the removal of the vaginal ring and stopping the estrogen patches.

Visit 18 (End of Study) includes a general medical examination, gynecological examination, vaginal echography, blood draw to determine hormone levels, general lab test (clinical chemistry, hematology, urinalysis, serum pregnancy test). The subject will be offered one cycle of oral contraceptives (not mandatory).

Visit 19 (Safety Follow-up) is by telephone 4 weeks after end of study treatment specifically to assess safety.

Criteria for Evaluation:

1. Pharmacokinetics:

Primary PK Parameters

Area under the curve from administration to last observed concentration of progesterone above the quantification limit (different from 0) at time t: (AUC0-t).

Area under the curve from administration to last draw at 408 h (AUC0-408h).

Maximum concentration obtained from serum concentrations of progesterone: (Cmax)

Concentration obtained from serum concentrations of progesterone at the last draw at 408 h (Cmin)

Mean Concentration, calculated as the value of AUC0-408h/administration interval (t). (Cav).

Secondary PK Parameters

Time to maximum concentration (Tmax)

Area under the curve extrapolated to infinite time: AUC0-∞

% FI calculated as FI=((Cmax−Cmin)/Cav)×100).

2. Pharmacodynamics:

Histological transformation of the endometrium after 14 days of treatment

Ultrasonographic endometrial features in response to hormonal treatment

3. Tolerability & Safety:

Evaluation of the incidence, intensity, duration and evolution of bleeding episodes Evaluation of the tolerability of the vaginal rings with evaluation of local symptoms and signs Evaluation of the acceptability of the vaginal rings Description of adverse events Results and Conclusions 1. Pharmacokinetic Results The serum concentrations of progesterone were tabulated per treatment, as shown in FIG. 4, and pharmacokinetic parameters were obtained or calculated from them. Pharmacokinetic parameters for each formulation are listed in the table below (mean value (SD))

| KINETIC PARAMETERS | T3 N = 8 | T4 N = 8 | T5 N = 8 |
| --- | --- | --- | --- |
| $C_{min}$ (ng/ml) | 2.07 (0.55) | 1.12 (0.20) | 0.57 (0.32) |
| $C_{max}$ (ng/ml) | 4.17 (0.89) | 3.43 (0.83) | 2.92 (0.39) |
| $C_{av}$ (ng/ml) | 2.61 (0.63) | 1.77 (0.46) | 0.70 (0.09) |
| $AUC_{0-4}$ (ng*h/ml) | 1059.95 (269.62) | 721.30 (188.80) | 282.02 (35.25) |
| $AUC_{0-406b}$ (ng*h/ml) | 1066.64 (256.83) | 724.15 (189.35) | 285.69 (38.00) |
| $AUC_{0-624b}$ (ng*h/ml) | 1266.52 (350.73) | 859.16 (184.19) | 371.66 (72.05) |
| $AUC_{0-\infty}$ (ng*h/ml) | 1921.16 (752.33) | 1165.80 (304.98) | 375.98 (71.31) |
| % Fluctuation | 80.96 (22.57) | 130.84 (27.29) | 339.62 (89.52) |
| $T_{1/2}$ (h) | 272.27 (117.18) | 262.99 (143.66) | 97.60 (36.96) |
| $T_{max}$ (h) | 27.00 (3.00-96.00) | 42.00 (3.00-144.00) | 12.00 (3.00-18.00) |

2. Pharmacodynamic Results

Histological Transformation of the Endometrium

Differences between the study treatments were noticed. A substantial endometrial transformation was observed with the T3 and T4 vaginal rings while it was feeble with the lowest dose ring T5, both according to the endometrial transformation scale and Noyes dating system. T3 was the only formulation that produced moderate or advanced endometrial transformation in all cases.

The differences between T3 and T4 vs T5 are statistically significant (p=0.004; p=0.011 respectively) while no significance is reached when comparing T3 vs T4.

Endometrial transformation scale results for each formulation are listed in the table below:

| Endometrial Transformation Scale | T3 Vaginal ring with 0.375 g of natural progesterone N (%) | T4 Vaginal ring with 0.125 g of natural progesterone Unit N (%) | T5 Vaginal ring with 0.040 g of natural progesterone N (%) |
| --- | --- | --- | --- |
| Grade 1 (absence of gestagenic effect) | 0 (0.0) | 0 (0.0) | 2 (28.6) |
| Grade 1-2 | 0 (0.0) | 1 (12.5) | 2 (28.6) |
| Grade 2 (weak gestagenic effect) | 0 (0.0) | 0 (0.0) | 2 (28.6) |
| Grade 3 (moderate gestagenic effect) | 1 (14.3) | 1 (12.5) | 0 (0.0) |
| Grade 4 (significant gestagenic effect) | 3 (42.9) | 3 (37.5) | 1 (14.3) |
| Grade 4-5 | 1 (14.3) | 3 (37.5) | 0 (0.0) |
| Grade 5 (full gestagenic effect) | 2 (28.6) | 0 (0.0) | 0 (0.0) |
| Total | 7 (100) | 8 (100) | 7 (100) |

3. Tolerability and Safety Results

Vaginal Bleeding

Some bleeding episodes were observed in women that received the vaginal rings during the first 14 days of treatment. All of the cases observed with T3 consisted of minor bleeding (spotting), while all severe bleeding episodes during this period were observed in women that received T4 and T5 treatments. In two volunteers under treatment with T4 and in 7 volunteers under treatment with T5, vaginal rings were prematurely removed due to severe vaginal bleeding. These patients prematurely discontinued the study, and the biopsy to evaluate the endometrial transformation was performed some days before the scheduled visit after 14 days of treatment. Of these 9 patients, only one of them, under treatment with T5, had low levels of serum estradiol by the time the biopsy had to be performed while all of them presented low levels of serum progesterone.

During the final days of the study (visits 17 and 18), severe withdrawal bleedings were observed in all treatment groups.

Tolerability

All of the women that were treated with the vaginal rings presented normal vaginal aspect in all visits. None of them presented with inflammation, erosion of vaginal mucosa, burning, dyspareunia, or other local signs and symptoms. Only one volunteer under treatment with T3 presented with moderate pain in a unique visit. None of the women that were treated with T4 and T5 referred discomfort or pruritus in any visit. Some discomfort was observed in women that received T3 (two women presented with mild discomfort in one of the study visits and one woman presented with moderate intensity discomfort in 3 study visits) and also some pruritus (mild intensity) but neither clinically relevant nor statistically significant between the treatments. The study participants tolerated well the three vaginal rings.

Acceptability

The three vaginal rings were well acceptable by study participants. No significant differences between the study treatments regarding tolerability, hygiene and convenience were observed.

Adverse Events

No serious adverse events were recorded during the study. Thirty-three (33) mild and three (3) moderate adverse events were reported with T3, twenty-eight (28) of them

CONCLUSIONS

Statistical significant differences among T3, T4 and T5 formulations are shown in the most relevant pharmacokinetic parameters analysed.

The linearity analyses show a less than proportional increase in pharmacokinetic parameters with increasing dose (from 0.040 to 0.375 g).

All the vaginal rings (0.375 g, 0.125 g and 0.04 g) produce gestagenic transformation of the endometrium due to the effect of the progesterone released from the rings.

There is a dose response effect regarding the gestagenic transformation of the endometrium when analysed histologically. Of the three doses tested, T3 (0.375 g) produced the highest gestagenic effect.

The systemic exposure of progesterone produced by the 0,375 g dose (T3) is of the same magnitude than that observed in the previous pharmacokinetic and pharmacodynamics study. In that study two higher doses were also analyzed (1.5 g and 0.75 g) and no differences in main pharmacokinetic parameters were shown among the three doses.

Considering the results of both studies the conclusion is that from a pharmacokinetic perspective the 0.375 g dose is the minimum studied dose producing the maximum progesterone systemic levels. In addition, in this study, the pharmacodynamic effect of the 0.375 g dose (T3) is of similar magnitude than that observed in the previous study, in which no differences were shown among the three doses tested (1.5 g, 0.75 g and 0.375 g) in their ability to produce endometrial gestagenic transformation. Considering the results of both studies, the conclusion is that from a pharmacodynamics perspective the 0.375 g (T3) dose corresponds to the minimal efficacious dose.

The bleeding pattern differed among the three tested treatments. Severe vaginal bleedings occurred during the second week of treatment with T4 and T5 while only minor spottings were observed with T3. Earlier severe bleedings were observed in women that received T5. Nine women (two receiving T4 and seven receiving T5) discontinued prematurely the study due to severe bleedings.

All the treatments presented a good tolerability/safety profile and did not reveal any unexpected adverse event. Most adverse events were mild and no differences among groups were evidenced.

Example 3

A Pharmacokinetic, Pharmacodynamics and Tolerability Study to Evaluate Three Vaginal Rings Containing 1.5 g, 0.75 g and 0.375 g of Natural Progesterone in Healthy Premenopausal Female Volunteers A clinical trial was conducted following the same methodology of Example 2. The serum concentrations of progesterone versus time are shown in FIG. 3.

Example 4

Progesterone Release Profiles

The progesterone release over time for a vaginal ring according to the present invention was compared to that of a vaginal ring comprising other polymorphic forms of progesterone.

Progesterone polymorph I (alpha) has a melting point of about 129° C. Where progesterone in polymorphic form I is employed for the preparation of the ring of the present invention, and a temperature above its melting point is employed during curing, it has been verified that the progesterone melts during the polymerization process and progesterone polymorph II (Beta) appears.

To verify how appearance of polymorph II can affect the final product, rings at temperatures under (120° C.) and above (150° C.) progesterone melting point were manufactured, with the composition described in Table I and method described below. Rings were then characterized and their progesterone in vitro release profiles were determined.

TABLE I

| Ring composition | |
|---|---|
| | % (w/w) |
| Progesterone | 8.5 |
| LSR DDR-4320. Part A | 45.8 |
| LSR DDR-4320. Part B | 45.8 |

For the manufacture, half of the progesterone was mixed with each part of the LSR and then both components were mixed and injected into the mold in which curing took place using different temperatures to obtain the rings: a first ring was cured at 120° C. (present invention) and the other ring was cured at 150° C. (comparative). Rings obtained were characterized using SEM, XRD and DSC. These techniques confirmed that only polymorph I appears when rings are manufactured under progesterone melting point, in contrast, polymorph I, II and other polymorphs, appear over the melting point.

Also, it was checked that rings cured at temperatures below progesterone melting point show in their surface some crystal particles, in contrast, rings manufactured at temperatures above the progesterone melting point show a sharp increase of progesterone crystals in the surface with different morphology and smaller size than the original API.

Regarding the progesterone in vitro profiles, the study was performed by placing the rings in IPA/water (60/40) at 37° C. using sink condition and using continuous stirring. Release was studied throughout 11 days. Progesterone was measured using a validated HPLC method. It was observed that rings cured at 150° C. had a higher burst effect and a higher release rate compared with rings cured at 120° C. (see Table II).

TABLE II

Cumulative release of progesterone (mg) over time

| Day | Rings cured at 120° C. | Rings cured at 150° C. |
| --- | --- | --- |
| 0 (4 h) | 37 ± 0 | 67 ± 2 |
| 1 | 106 ± 1 | 144 ± 2 |
| 2 | 150 ± 1 | 192 ± 3 |
| 3 | 180 ± 2 | 224 ± 3 |
| 4 | 206 ± 1 | 251 ± 3 |
| 7 | 260 ± 2 | 306 ± 3 |
| 8 | 275 ± 2 | 319 ± 3 |
| 9 | 287 ± 2 | 329 ± 3 |
| 10 | 297 ± 1 | 336 ± 2 |
| 11 | 308 ± 1 | 344 ± 2 |

The invention claimed is:

1. Intravaginal ring comprising progesterone, wherein at least about 75% of said progesterone is in polymorphic form I.

2. Intravaginal ring according to claim 1, wherein at least about 95% of said progesterone is in polymorphic form I.

3. Intravaginal ring according to claim 1, comprising from 17.4% to 2.9% wt progesterone with respect to the total weight of the ring.

4. Intravaginal ring according to claim 3, comprising from 11.6% to 2.9% wt progesterone with respect to the total weight of the ring.

5. Intravaginal ring according to claim 4, comprising from 8.7% to 2.9% wt progesterone with respect to the total weight of the ring.

6. Intravaginal ring according to claim 1, comprising from 0.75 to 0.100 g progesterone.

7. Intravaginal ring according to claim 6, comprising from 0.50 to 0.125 g progesterone.

8. Intravaginal ring according to claim 7, comprising from 0.375 to 0.125 g progesterone.

9. Intravaginal ring according to claim 1, further comprising a polymeric composition as pharmaceutically acceptable carrier.

10. Intravaginal ring according to claim 9 further comprising at least one silicone-based elastomer as pharmaceutically acceptable carrier.

11. Intravaginal ring according to claim 1, wherein the intravaginal ring has an outer diameter of about 50 to about 60 mm and a cross-sectional diameter of about 5 to about 8 mm.

12. Process for making the vaginal ring as defined in claim 1, comprising the steps of:
   a) Mixing progesterone, wherein at least 75% of the progesterone is in polymorphic form I, with a pharmaceutically acceptable polymeric composition;
   b) Curing the mixture resulting from step a) at a temperature of 120° C. or lower.

13. Process according to claim 12, wherein the pharmaceutically acceptable polymeric composition comprises a vinyl dimethyl endblocked polysiloxane, a hydride dimethyl endblocked polysiloxane, a catalyst which promotes hydrosililation and a catalyst inhibitor.

14. Method for treating infertility in a female subject in need thereof, wherein the female subject is a human, the method comprising administering to the female subject an intravaginal ring, the intravaginal ring comprising:
   a therapeutically effective amount of progesterone, wherein at least 75% of said progesterone is in polymorphic form I;
   a pharmaceutically acceptable carrier.

15. Method according to claim 14, wherein the treatment of infertility is an assisted reproductive technique.

16. Method according to claim 15, wherein the treatment of infertility comprises a luteal phase support.

17. Method according to claim 14, wherein the intravaginal ring is not replaced for a period of at least 14 days.

* * * * *